US00PP15412P2

(12) United States Plant Patent
Wain

(10) Patent No.: US PP15,412 P2
(45) Date of Patent: Dec. 7, 2004

(54) ***CHRYSANTHEMUM* PLANT NAMED 'YOTOBAGO'**

(50) Latin Name: *Chrysanthemum×morifolium*
Varietal Denomination: Yotobago

(75) Inventor: Peter Wain, Southampton (GB)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/787,050

(22) Filed: Feb. 25, 2004

(51) Int. Cl.[7] ..... A01H 5/00

(52) U.S. Cl. ..... Plt./293

(58) Field of Search ..... Plt./293

*Primary Examiner*—Anne Marie Grunberg
(74) *Attorney, Agent, or Firm*—C. A. Whealy

(57) ABSTRACT

A new and distinct cultivar of *Chrysanthemum* plant named 'Yotobago', characterized by its uniform and outwardly spreading plant habit; strong and freely branching growth habit; dark green-colored foliage; uniform flowering response and habit; typically grown as a spray-type; early flowering habit; decorative-type inflorescences; intense velvety red-colored ray florets that resist fading under low and high temperatures; and good postproduction longevity with plants maintaining good substance and color for about four to five weeks in an interior environment.

2 Drawing Sheets

Botanical classification/cultivar designation: *Chrysanthemum×morifolium* cultivar Yotobago.

BACKGROUND OF THE INVENTION

The present Invention relates to a new and distinct cultivar of *Chrysanthemum* plant, botanically known as *Chrysanthemum×morifolium* and hereinafter referred to by the name 'Yotobago'.

The new *Chrysanthemum* is a product of a planned breeding program conducted by the Inventor in Fareham, Hampshire, United Kingdom. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made by the Inventor in January, 1999, in Fareham, Hampshire, United Kingdom, of a proprietary *Chrysanthemum* seedling selection identified as code number P101B4, not patented, as the female, or seed, parent with a *Chrysanthemum* selection identified as RGI, not patented, as the male, or pollen, parent. The new *Chrysanthemum* was discovered and selected by the Inventor in September, 1999, as a single flowering plant from within the resulting progeny of the stated cross-pollination grown in a controlled environment in Fareham, Hampshire, United Kingdom.

The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new *Chrysanthemum* by vegetative tip cuttings was first conducted in Fareham, Hampshire, United Kingdom in December, 1999. Asexual reproduction by cuttings has shown that the unique features of this new *Chrysanthemum* are stable and reproduced true to type in successive generations.

SUMMARY OF THE INVENTION

The cultivar Yotobago has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yotobago'. These characteristics in combination distinguish 'Yotobago' as a new and distinct *Chrysanthemum*:

1. Uniform and outwardly spreading plant habit.
2. Strong and freely branching growth habit.
3. Dark green-colored foliage.
4. Uniform flowering response and habit.
5. Typically grown as a spray-type.
6. Early flowering, eight week response time.
7. Decorative-type inflorescences.
8. Intense velvety red-colored ray florets that resist fading under low and high temperatures.
9. Good postproduction longevity with plants maintaining good substance and color for about four to five weeks in an interior environment.

Plants of the new *Chrysanthemum* differ from plants of the parent selections in plant growth habit and ray floret coloration.

Plants of the new *Chrysanthemum* can be compared to plants of the cultivar Red Delano, disclosed in U.S. Plant Pat. No. 8,345. In side-by-side comparisons conducted in Fort Myers, Fla., plants of the new *Chrysanthemum* differed from plants of the cultivar Red Delano in the following characteristics:

1. Plants of the new *Chrysanthemum* were more uniform and not as outwardly spreading as plants of the cultivar Red Delano.
2. Plants of the new *Chrysanthemum* had smaller inflorescences than plants of the cultivar Red Delano.

3. Ray florets of plants of the new *Chrysanthemum* were brighter red than ray florets of plants of the cultivar Red Delano.

Plants of the new *Chrysanthemum* can also be compared to plants of the cultivar Cherry Pomona, disclosed in U.S. Plant Pat. No. 7,850. In side-by-side comparisons conducted in Fort Myers, Fla., plants of the new *Chrysanthemum* differed from plants of the cultivar Cherry Pomona in the following characteristics:

1. Plants of the new *Chrysanthemum* were more uniform and not as outwardly spreading as plants of the cultivar Cherry Pomona.
2. Plants of the new *Chrysanthemum* had smaller inflorescences than plants of the cultivar Cherry Pomona.
3. Ray florets of plants of the new *Chrysanthemum* were brighter red than ray florets of plants of the cultivar Cherry Pomona.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yotobago' grown as a spray-type.

The photograph on the second sheet comprises a close-up view of typical inflorescences of 'Yotobago' grown as a spray-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yotobago.

Commercial classification: Decorative-type potted *Chrysanthemum.*

Parentage:

*Female, or seed, parent.*—Proprietary *Chrysanthemum×morifolium* seedling selection identified as code number P101B4, not patented.

*Male, or pollen, parent.*—Proprietary *Chrysanthemum×morifolium* selection identified as RGI, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted *Chrysanthemum* typically grown as a spray-type. Upright with lateral branches outwardly spreading; uniformly mounded crown. Strong and freely branching growth habit; about three or four lateral branches develop after removal of terminal apex (pinching); dense and full plants.

*Plant height.*—About 27 cm.

*Plant width.*—About 39 cm.

*Lateral branches.*—Length: About 21 cm. Diameter: About 4 mm. Internode length: About 1 cm. Strength: Strong. Texture: Pubescent. Color: Close to 146A.

*Foliage description.*—Arrangement: Alternate; simple. Length: About 7.4 cm. Width: About 4.6 cm. Apex: Mucronate. Base: Attenuate. Margin: Palmately lobed, sinuses between lateral lobes parallel to divergent. Texture, upper and lower surfaces: Pubescent. Color: Developing foliage, upper surface: Darker than 147A. Developing foliage, lower surface: Darker than 147B. Fully expanded foliage, upper surface: Close to 147A. Fully expanded foliage, lower surface: Close to 147B. Venation, upper surface: Close to 147A. Venation, lower surface: Close to 147B. Petiole length: About 2.2 cm. Petiole diameter: About 4 mm. Petiole color, upper surface: Close to 146A. Petiole color, lower surface: Close to 146A to 146B.

Inflorescence description:

*Appearance.*—Decorative-type inflorescence form with elongated oblong-shaped ray florets. Inflorescences borne on terminals above foliage. Disk and ray florets develop acropetally on capitulum. Inflorescences not fragrant. Plants typically grown as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about four to five weeks in an interior environment.

*Quantity of inflorescences.*—About seven inflorescences develop per lateral branch.

*Inflorescence bud.*—Height: About 5 mm. Diameter: About 6 mm. Shape: Oblate. Color: Close to 146A.

*Inflorescence diameter.*—About 5.75 cm.

*Inflorescence depth (height).*—About 2.2 cm.

*Diameter of disc.*—No disc florets observed.

*Receptacle diameter.*—About 5 mm.

*Ray florets.*—Shape: Elongated oblong. Orientation: Initially upright, then perpendicular to the peduncle. Aspect: Straight, concave. Length: About 2.8 cm. Corolla tube length: About 7 mm. Width: About 7 mm. Apex: Emarginate. Base: Fused into a corolla tube. Margin: Entire. Texture: Smooth, glabrous, velvety. Number of ray florets per inflorescence: About 177 arranged in numerous whorls. Color: When opening, upper and lower surfaces: 187A to 187B. Fully opened, upper surface: Close to 9A heavily overlain with closer to 53A; color does not fade under low or high temperatures. Fully opened, upper surface: Close to 9B heavily underlain with closer to 53A; color does not fade under low or high temperatures. Disc florets: No disc florets observed.

*Phyllaries.*—Quantity per inflorescence: About 30. Length: About 7 mm. Width: About 3 mm. Shape: Deltoid. Apex: Acute. Base: Truncate. Margin: Entire. Texture, upper surface: Waxy, smooth. Texture, lower surface: Pubescent. Color, upper surface: Close to 146A to 146B. Color, lower surface: Close to 146A.

*Peduncles.*—Length: First peduncle: About 4.8 cm. Fourth peduncle: About 6 cm. Seventh peduncle: About 7.8 cm. Diameter: About 2 mm. Angle to vertical: About 45° from vertical. Strength: Strong, flexible. Texture: Pubescent. Color: Closest to 146A.

*Reproductive organs.*—Gynoecium: Style color: Close to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yotobago', as illustrated and described.

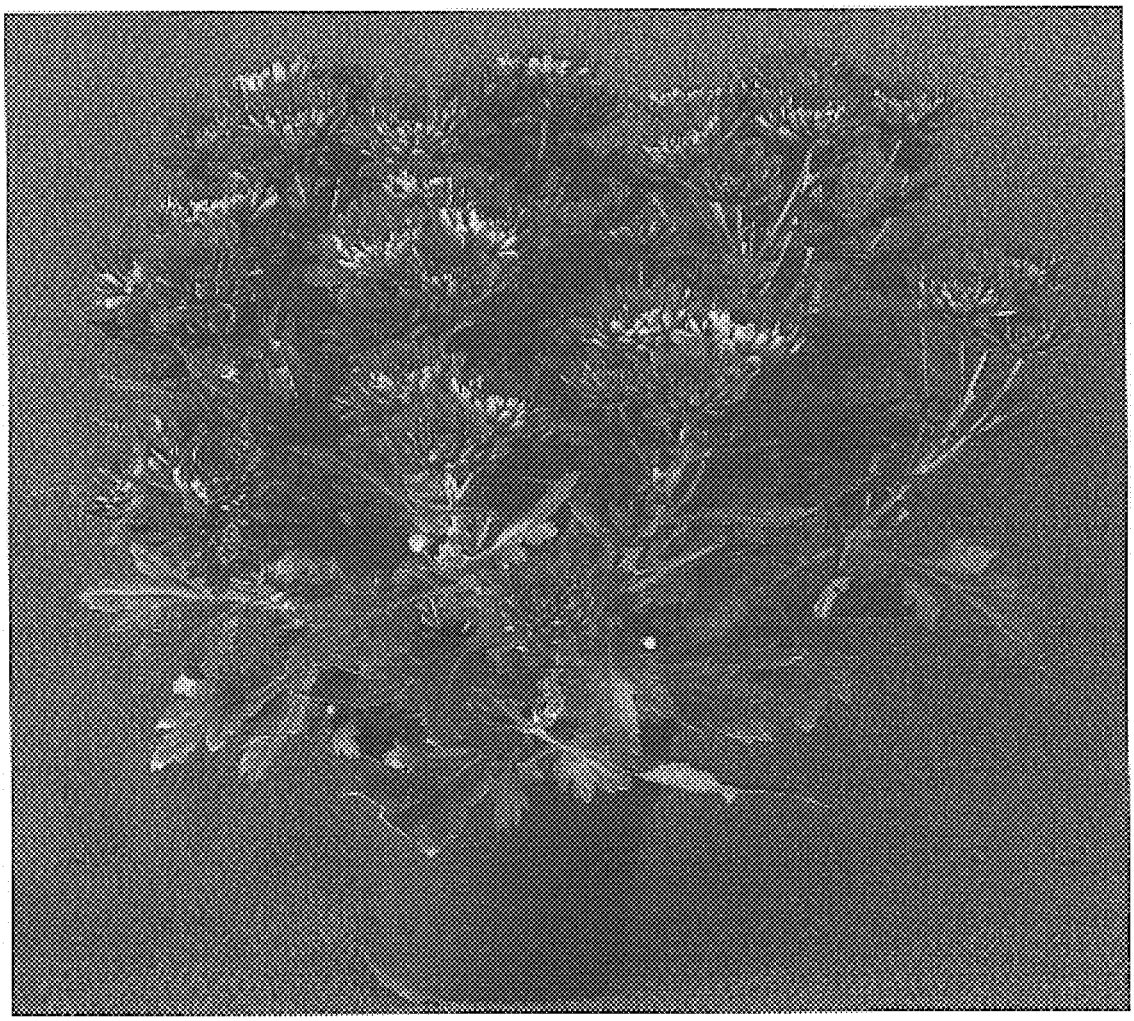

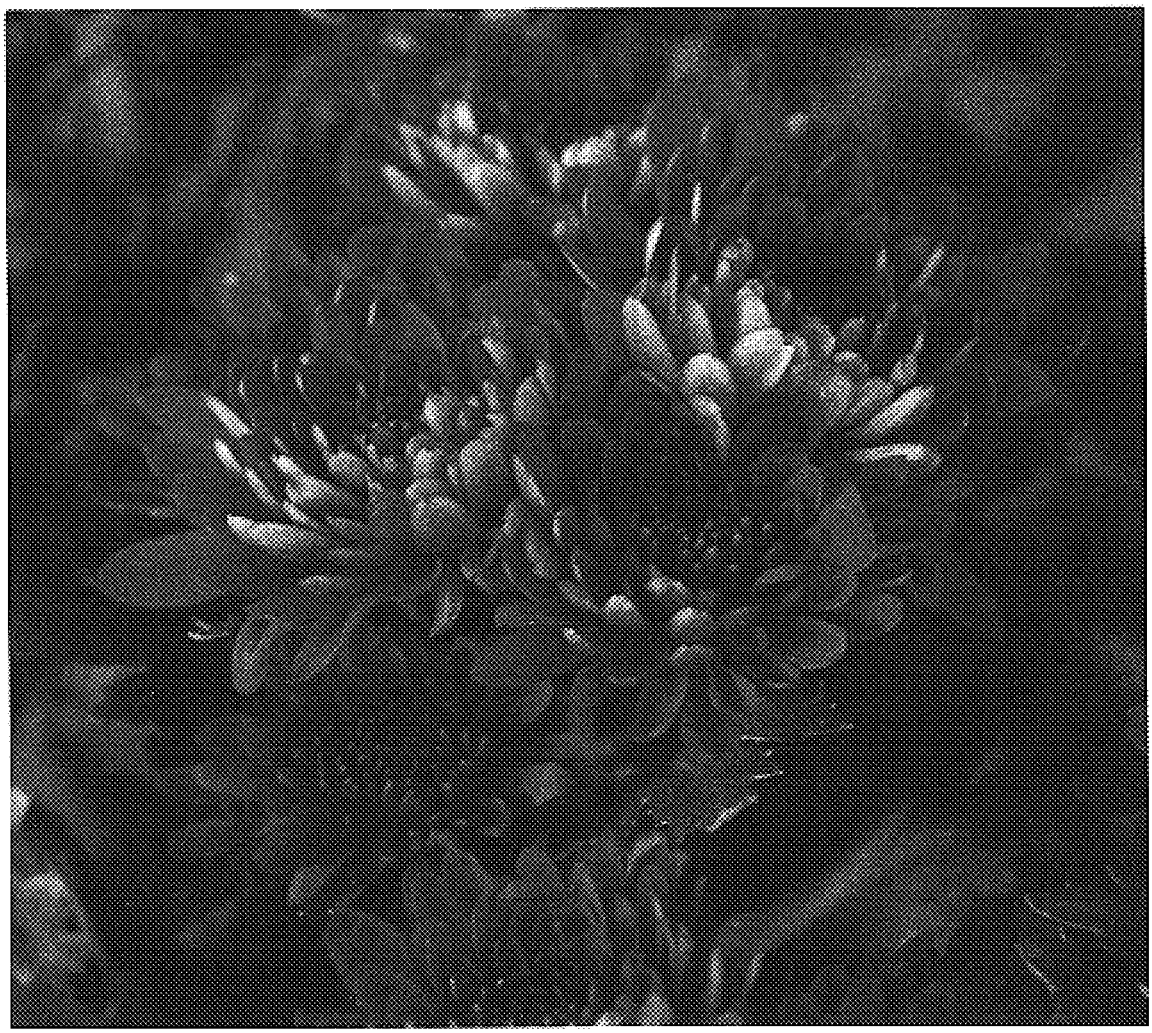

* * * * *